United States Patent [19]
O'Donnell et al.

[11] Patent Number: 6,050,713
[45] Date of Patent: Apr. 18, 2000

[54] INTRAVENOUS DRIP LIGHTING DEVICE

[76] Inventors: Joan O'Donnell, 78 High St., Wilmington, Mass. 01887; Michael J. Slejzer, 398 Andover St., Georgetown, Mass. 08133

[21] Appl. No.: 09/081,535

[22] Filed: May 19, 1998

Related U.S. Application Data

[60] Provisional application No. 60/056,645, Aug. 22, 1997.

[51] Int. Cl.[7] ...................................................... F21V 8/00
[52] U.S. Cl. ........................ 362/551; 362/572; 362/804; 362/431; 362/418
[58] Field of Search .................. 604/253; 73/861.41; 362/551, 554, 572, 418, 431, 410, 413, 414, 285, 396

[56] References Cited

U.S. PATENT DOCUMENTS

| | | | |
|---|---|---|---|
| 3,590,809 | 7/1971 | London | 604/253 |
| 3,690,318 | 9/1972 | Gursuch | 604/253 |
| 4,453,204 | 6/1984 | Warshawsky | 604/396 |
| 5,351,168 | 9/1994 | Easley . | |
| 5,425,730 | 6/1995 | Luloh . | |
| 5,843,045 | 12/1998 | DuPont | 604/251 |

OTHER PUBLICATIONS

Catalog From Lighting Services Inc. Entitled "Fiber Optic Lighting" Apr. 1994.
Invention Disclosure Form DTD Jun. 2, 1997 Showing Reduction to Practice on May 1, 1997.

*Primary Examiner*—Thomas M. Sember
*Attorney, Agent, or Firm*—Lambert & Associates, PLLC; Randolph P. Calhoune; Scott B. Garrison

[57] ABSTRACT

The specification relates to a means of illuminating the drip chamber of intravenous bags during medical processes that are performed in a darkened atmosphere. The apparatus uses an adjustable pole that supports an intravenous bag support that is capable of holding multiple bags and a plate that supports a fiber optic light housing which illuminates all drip chambers adequately and equally and with differing colored light if necessary for distinction. The apparatus is attachable to a procedure table using an adjustable attachment means. The light housing position is fully adjustable in relation to it's target.

11 Claims, 4 Drawing Sheets

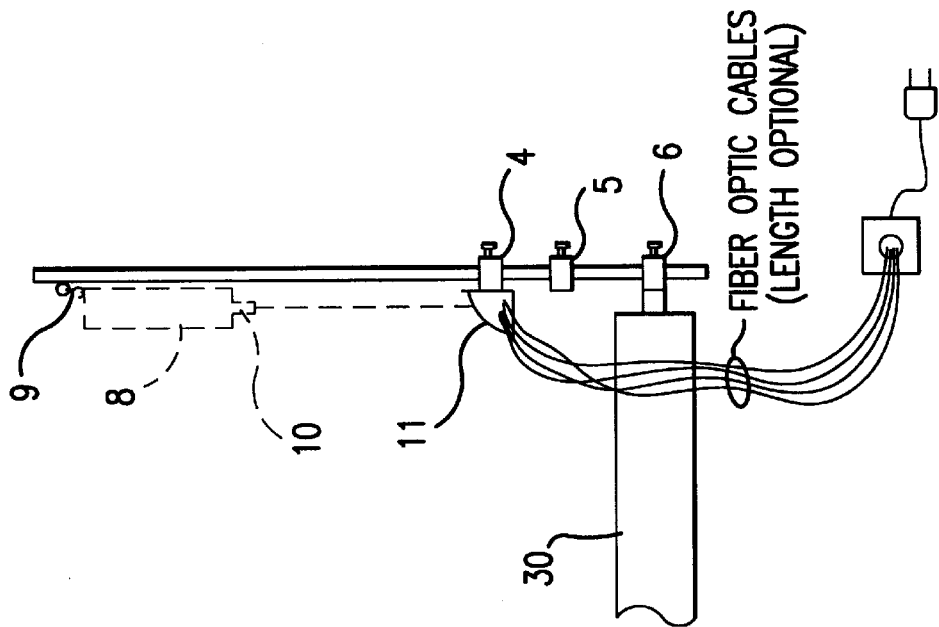
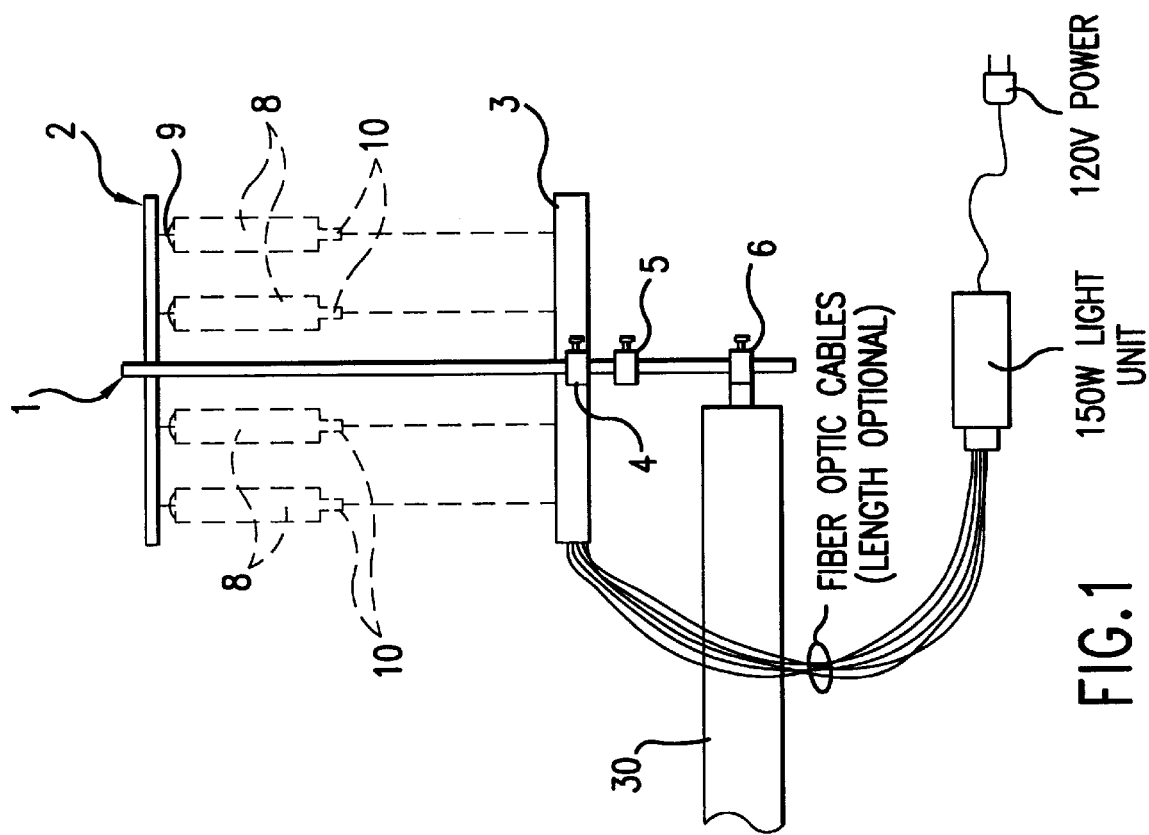

INTRAVENOUS DRIP LIGHTING DEVICE

CROSS REFERENCE TO RELATED APPLICATIONS

This application claims the benefit of the filing date of Provisional Patent application Ser. No. 60/056,645 filed Aug. 22, 1997, by the same inventors.

BACKGROUND OF THE INVENTION

The present invention relates to an illumination device for use during interventional or diagnostic procedures. More specifically, this device is used during interventional or diagnostic procedures to illuminate intravenous (IV) drip chambers.

The inventors of the present invention have solved the common problem of not being able to provide direct continuous lighting to a radiologist or interventional radiologist during an interventional or diagnostic procedure. More specifically, the present invention provides direct continuous lighting onto an IV drip chamber using a fiber optic light source. This is an important feature of the present invention because invasive interventional or diagnostic procedures are typically performed using fluoroscopy, in a dark room or a room with only ambient lighting since any direct light will compromise the performance of the radiologist, or integrity of the procedure, with resulting increased risk to the patient. The medical team must be able to clearly view the IV drip chamber and confirm a constant fluid drip is being maintained in order to prevent a life-threatening clot from forming at the tip of a catheter which is utilized throughout the interventional procedure. The present invention provides a localized light source that is accurately directed at the IV drip chamber using a fiber optic light source, and therefore works well in dimmed room light. Thus, the device does not interfere with an operation performed during fluoroscopy.

Heretofore, several attempts have been made to address this problem. U.S. Pat. No. 5,425,730 to Luloh discloses an illumination cannula system for vitreous surgery, said cannula system having a plurality of illuminated cannula ports, each including a multiplicity of optical fibers annularly arranged about a central conduit channel provided with a double seal onto which a sleeve connector or boot of an infusion line adapter or sealing plug can be attached. The adapter includes an extended tube for discharging fluid beyond the termination of the fibers. The double seal provides a convenient, positive snap-action sealing connection. Identical configurations of the cannula ports enable post-placement selection and interchange of infusion and instrumentation ports. This patent, however, does not teach use of IV drip illumination practiced in the present invention.

Further prior art includes U.S. Pat. No. 5,351,168 to Easley discloses an illumination device for use in surgery on the human body that has an optical fiber which terminates distally in a bullet-shaped tip. The tip has an exterior surface which is a surface of revolution of a predetermined curve about the longitudinal axis of the tip, the predetermined curve having a first proximal segment, a second intermediate segment, and a third distal segment. The first segment has tangents substantially all of which make less than a first predetermined angle with the longitudinal axis. The second segment has tangents substantially all of which make angles with the longitudinal axis which are greater than the first predetermined angle and less than a second predetermined angle. The third segment has tangents substantially all of which make angles with the longitudinal axis which are greater than the second predetermined angle. A method of manufacturing the tip is disclosed as well. Again, this invention does not teach use of the illumination devices in conjunction with an IV pole secured with clamps created for the purpose of illuminating IV drip chambers.

SUMMARY OF THE INVENTION

The present invention is directed to an illumination device for use during an interventional or diagnostic procedure to illuminate intravenous drip chambers that are laterally arranged, and solves the above mentioned problems.

In a preferred version, the present invention provides a device to illuminate IV solution drip chambers and IV solution drips, during an interventional or diagnostic procedure. These IV solution drips (up to 4 at a time) need to be constantly monitored by a medical team while the procedure is in progress. This monitoring of the IV chambers is critical because the chambers flush a sheath that is placed in the patient's groin area, thus allowing the surgeon to guide a catheter through a patient's artery to the brain, spinal cord, or other location depending upon the nature of the particular radiological procedure. This is a very demanding and tedious task for the medical team because the procedure may continue for 8 hours at one sitting, and the medical team must keep a watchful eye on the drips for the full period of the procedure. More importantly, these procedures are typically performed in a hospital radiology suite in which the procedures, for specific technical reasons, must be carried out under fluoroscopy while the procedure room lights are turned off, or dimmed to some low light level.

Initially, in order to alleviate the above-described problem, the inventors utilized flashlights taped to the end of the procedure table to illuminate the IV drips. This method proved to be impractical because the flashlights were not stable, and tended to fall off the table if the table was repositioned. Also, the batteries used as a power source for the flashlight would fully diminish their charge after two or three hours, with the expected loss of illuminating power for the flashlight bulb.

Another problem overcome by the inventors was when the IV bags were placed on a pole with four hooks situated in a square position, and not parallel to each other, the light would illuminate in an uneven manner, lighting one of the IV chambers more than the others, with the IV bags located in the front blocking the view of the IV bags located in the back. Consequently, an IV chamber could cease dripping, and the technician would not be able to discern the cessation of the flow. In this situation, a patient could be severely injured.

As a result of the above, the inventors have developed a safe and efficient device that solves the problems mentioned. As will be made clear from the drawings presented below, the preferred configuration of the invention utilizes a fiber optic light source in conjunction with an adjustable intravenous pole connected by a plurality of clamps in order to effectively illuminate IV drip chambers in an interventional suite with low or non existent lighting

BRIEF DESCRIPTION OF THE DRAWINGS

These and other features, aspects, and advantages of the present invention will become better understood with reference to the following description, appended claims, and accompanying drawings where:

FIG. 1 is a rear view of the present invention where the light housing comprises a plurality of light sources and a light unit connected by fiber optic cables. The adjustable intravenous pole can be made of rigid material, metal, or any similar type of material that will allow the pole to support IV bags in an upright position. The adjustable attachment means serve to hold the IV pole securely in an upright position;

FIG. 2 is a side view of the invention where the adjustable attachment means mounts to the back of a plate secured to the IV pole, and allows for vertical adjustment of the light housing with respect to the IV drip chambers.

DETAILED DESCRIPTION OF THE PREFERRED EMBODIMENTS

Figure 3:
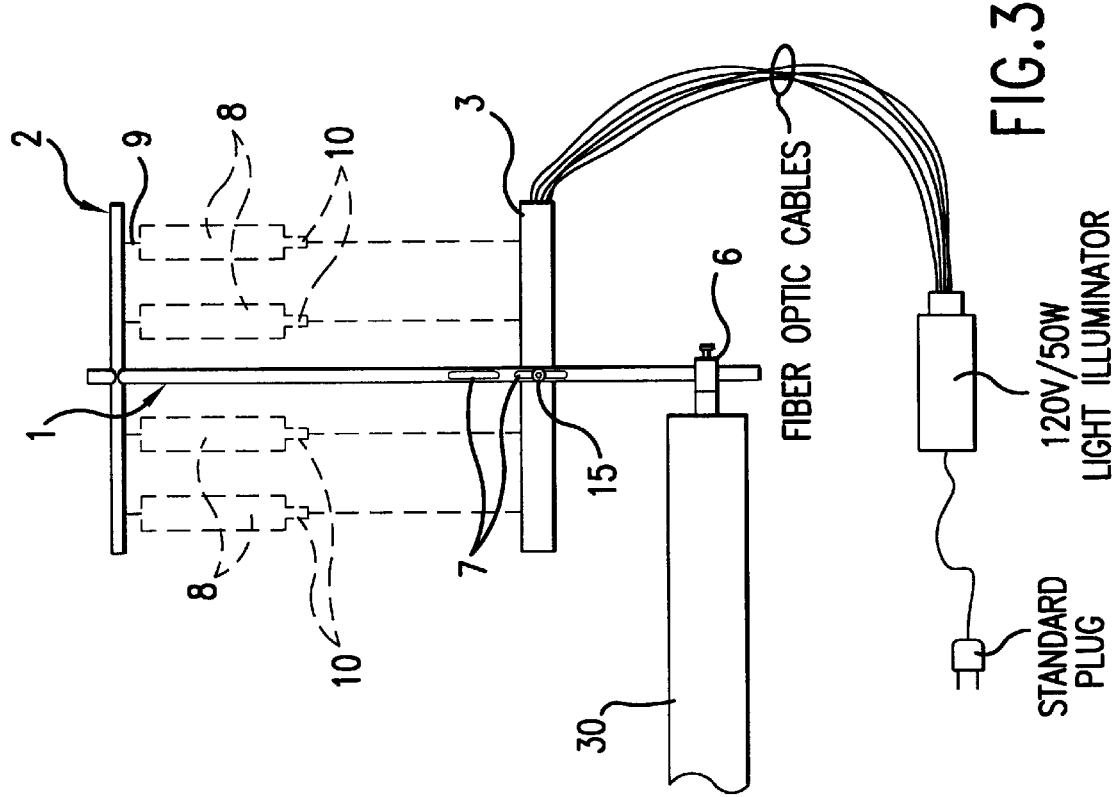
FIG. 3 is a rear view of another embodiment of the present invention, similar to FIG. 1, but with a trough configuration holding the fiber optic light housing. This view also shows another preferred method of light housing attachment and adjustment.

With reference to FIGS. 1 and 3, the preferred embodiment has an adjustable pole 1 that attaches the remainder of the invention's components to a procedure table or bed 30 using an adjustable attachment means 6. Adjustable attachment means 6 is contemplated by applicant to be any mechanism that will rigidly and securely attach a pole to a table or bed 30 and be vertically adjustable. Attached perpendicularly to the top of pole 1 is an IV bag support 2. FIG. 5 shows the components of one preferred embodiment of this attachment. In this embodiment, the top end of adjustable pole 1 is convex in shape to match the round IV bag support 2 with a tapped hole placed in the center of and perpendicular to the convex area and concentric to the outer diameter of the pole. End cap 12 is also convex in shape to fit the IV bag support 2 but has a hole through the center of and perpendicular to the convex face and concentric to outer diameter of cap. IV bag support 2 also has a hole drilled through the mid point of its length and perpendicular to its outer diameter. By using a threaded fastener 13 positioned through first the end cap 12, followed by the IV bag support center hole and tightened into the threaded hole of pole 1, assembly of the upright portion of the invention is completed quickly and with a minimum of tools. Once again as shown in FIGS. 1 and 3, the IV bag support 2 comprises a horizontal bar with a plurality of hooks 9 suspended downward and spaced proportionately across the bar to accommodate hanging a plurality of IV bags 8. At a position on pole 1, below the length of an IV bag 8 with drip chamber 10 hung from IV bag support 2 and above adjustable attachment means 6, is attached light housing support plate 3 horizontally and perpendicularly to pole 1. This plate supports the light housing 11, shown in FIGS. 2 and 4, such that it fully illuminates a plurality of drip chambers 10. In one preferred embodiment of the invention the support plate 3 is adjustable in height by using adjusting clamp 4 shown in FIGS. 1 and 2. This adjusting clamp can be any type of clamp, such as a bar clamp, that slides up and down on pole 1 and is tightened into position without the need for additional tools, one such way would be by use of a thumb screw. The ability to slide the support plate to a plurality of heights with respect to IV drip chamber 10 allows for precise lighting of the IV drip chambers 10 that is otherwise not available during a procedure needing limited light such as fluoroscopy. Directly beneath adjusting clamp 4 is a safety clamp 5 which is of similar configuration as clamp 4. Should the adjusting clamp fail to be tightened sufficiently and in the event it lets loose, the clamp and support plate will converge on the safety clamp 5 which will prevent the assembly from falling down pole 1.

Figure 4:
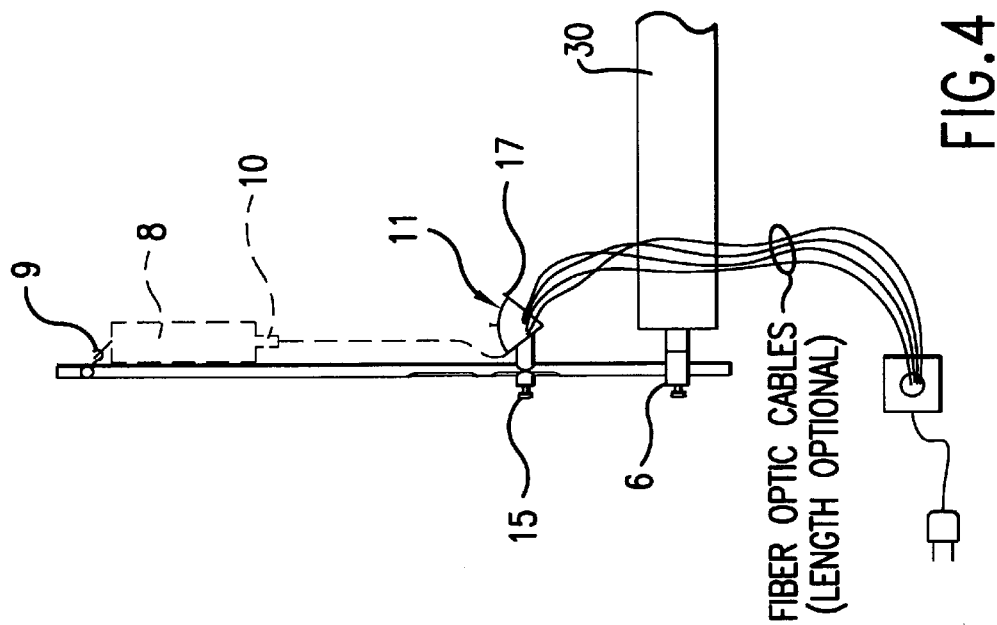
FIG. 4 is a side view of the FIG. 3 embodiment.
Figure 5:
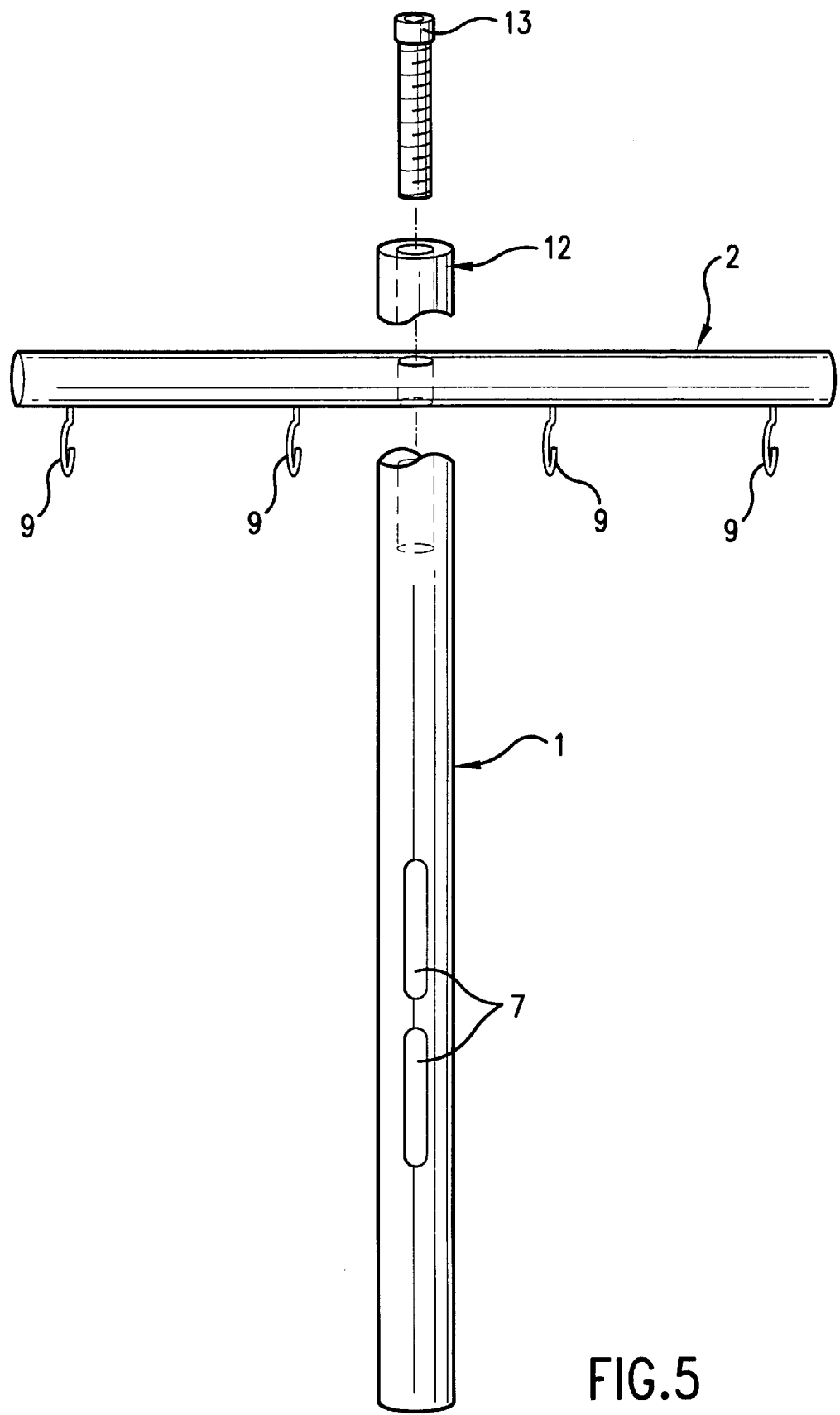
FIG. 5 is an exploded view of the IV pole portion of the present invention.
Figure 6:
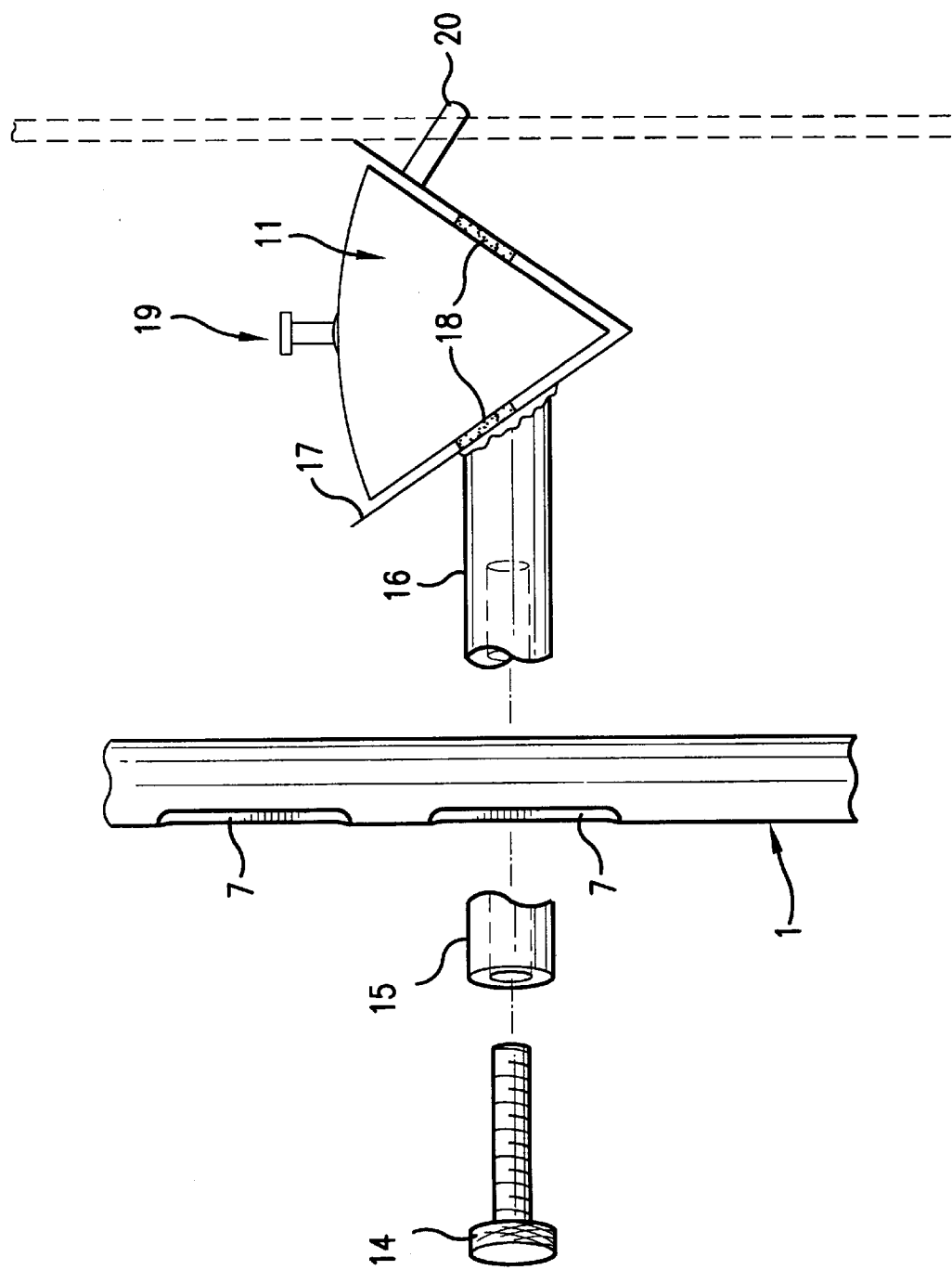
FIG. 6 is an exploded view of the "V" shaped trough light bar support plate of the FIG. 3 embodiment.

In an alternative embodiment of the invention, shown in FIGS. 4 and 6, the light housing is supported using the support plate 3 which is shaped into a "V" shaped trough identified as item 17. Although there are many configurations of plate that can be used, it is necessary that it support the light housing in such a way that the light source is directed upward and illuminating the IV drip chambers 10 without the possibility of movement after final adjustment. The trough is adjustable up and down on IV pole 1 using two adjustment slots 7 shown in FIG. 3. With the slot configuration, a backup safety clamp is not necessary due to the slot bottom preventing the bar from sliding down to any significantly damaging distance. Similar to the assembly of the IV bag support 2 to the pole 1, the support plate 17 is attached to pole 1, as referenced in FIG. 6. A thumb screw is tightened through cap 15, one of two slots 7, and into the tapped hole of lug 16 of the support plate 17 at the desired height. Lug 16 is welded onto one side of the "V" shaped support plate 17 and IV tubing clips 20 are attached to the opposite outer side of the trough. The clips hold the IV tubing in place to prevent air bubbles from inadvertently forming in the IV drip chambers as the procedure table is moved in various directions by the attending physician, nurse, or technician.

The light housing 11 supplies a multiple of fiber optic light sources depending on illumination needs. The light sources must illuminate only the IV drip chambers and not supply excess light that may interfere with the limited light medical procedure. The fiber optic light sources are important components of the invention whereby they are flexible and can be manipulated to direct the light to a specific target. They also transmit only light and do not deliver unwanted heat to their target. The light housing contains the light emitting end of the fiber optic cable. The opposite end of the cable is connected to its power source which is powered from a remote source. An alternative embodiment of the invention, shown in FIG. 6, has the light housing 11 held in support plate 3 using hook and loop type fasteners such as the product commonly known as VELCRO shown as tabs 18. The light housing can also accommodate various colored lens 19 on the fiber optic light sources to facilitate viewing particular IV chambers during a procedure. The fiber optic cables can be of the glass or plastic type.

The inventors contemplate the embodiment as being made of any type of material able to support and hold rigidly a plurality of IV bags and their corresponding components which includes the drip chamber and tubing along with the required light source.

Each of the above embodiments describe several configurations and variations of the same. However, the invention, although it may have an infinite number of design configurations possesses certain recurring characteristics. The characteristics that define the invention are; that the material used must be rigid and have sufficient strength to support all components, that the adjustable attachment means allows for adjustability of both the pole height with respect to the procedure table and the light housing height with respect to the IV drip chambers, that the light housing support plate be able to support a plurality of light sources while directing them to their desired illumination point, that it supports a plurality of IV bags in a horizontal line, and that it be able to mount rigidly to a procedure table or bed. Accordingly, this invention is not limited to the particular embodiments disclosed, but is intended to cover all modifications that are within the spirit and scope of the invention as defined by the appended claims.

What is claimed is:

1. An apparatus for illuminating an intravenous drip chamber comprising:

a pole;

a plurality of adjustable attachment means, wherein said pole is attachable in a vertical position to a procedure table using said adjustable attachment means;

an intravenous bag support, wherein said intravenous bag support is horizontally and rigidly mounted to said pole;

a light housing support plate, wherein said light housing support plate is mounted horizontally and perpendicular to said pole below said intravenous bag support using said adjustable attachment means;

a light housing, wherein said light housing is supported horizontally on said light housing support plate.

2. An apparatus according to claim 1 wherein said intravenous bag support comprises a plurality of hooks such that said hooks are linear and parallel along said support and spaced sufficiently to accommodate a plurality of intravenous bags hung in parallel.

3. An apparatus according to claim 1 wherein said light housing comprises a plurality of fiber optic light sources arranged in a linear pattern within said light housing.

4. An apparatus according to claim 3 wherein said light housing further comprises a movable fiber optic light source lenses of various colors.

5. An apparatus according to claim 1 wherein said adjustable attachment means of said pole further comprises a first plurality and a second plurality of clamping means arranged one above the other on said pole for safety in the event one of the two plurality of clamping means fails.

6. An apparatus according to claim 1 wherein said adjustable attachment means of said light housing support plate further comprises a first plurality and a second plurality of clamping means arranged one above the other on said pole for safety in the event one of the two plurality of clamping means fails.

7. An apparatus for illuminating an intravenous drip chamber comprising:

a pole;

a plurality of adjustable attachment means, vertically attaching said pole to a procedure table;

an intravenous bag support horizontally and rigidly mounted to said pole, said intravenous bag support comprises a plurality of hooks such that said hooks are linear and parallel along said support and spaced sufficiently to accommodate a plurality of intravenous bags hung in parallel;

a light housing support plate mounted horizontally and perpendicular to said pole below said intravenous bag support using said adjustable attachment means; and a light housing horizontally supported on said light housing support plate.

8. An apparatus according to claim 7 wherein said light housing comprises a plurality of fiber optic light sources arranged in a linear pattern within said light housing.

9. An apparatus according to claim 7 wherein said light housing comprises a plurality of fiber optic light sources arranged in a linear pattern within said light housing.

10. An apparatus according to claim 7 wherein said adjustable attachment means further comprises a first plurality and a second plurality of clamping means arranged one above the other on said pole for safety in the event one of the two plurality of clamping means fails.

11. An apparatus according to claim 7 wherein said adjustable attachment means of said light housing support plate further comprises a first plurality and a second plurality of clamping means arranged one above the other on said pole for safety in the event one of the two plurality of clamping means fails.

* * * * *